United States Patent [19]
Potter et al.

[11] Patent Number: 6,149,873
[45] Date of Patent: Nov. 21, 2000

[54] COMPUTER GAME ENHANCEMENT

[76] Inventors: Mike Potter, 1619 W. Morningside Dr., San Bernardino, Calif. 92407; Scott Raines, 3600 Amberwood Ct., Lake Elsinore, Calif. 92530

[21] Appl. No.: 09/078,627

[22] Filed: May 14, 1998

[51] Int. Cl.[7] .................................................... A62B 7/08
[52] U.S. Cl. .......................... 422/123; 239/271; 239/272; 422/122; 422/124
[58] Field of Search ..................... 422/122, 123, 422/124, 5; 239/271–272, 309, 311

[56] References Cited

U.S. PATENT DOCUMENTS

| | | | |
|---|---|---|---|
| 2,905,049 | 9/1959 | Laube | 422/5 |
| 5,071,621 | 12/1991 | Tokuhiro et al. | 422/5 |
| 5,591,409 | 1/1997 | Watkins | 422/123 |
| 5,610,674 | 3/1997 | Martin | 352/85 |
| 5,833,929 | 11/1998 | Watson et al. | 422/23 |
| 5,898,475 | 4/1999 | Martin | 352/85 |

*Primary Examiner*—Krisanne Thornton

[57] ABSTRACT

A scent apparatus is provided including a scenting mechanism for dispensing a scent upon the actuation thereof. Further included is an actuation mechanism connected between the scenting mechanism and either a computer or a game unit for actuating the scenting mechanism during a game.

6 Claims, 2 Drawing Sheets

COMPUTER GAME ENHANCEMENT

BACKGROUND OF THE INVENTION

1. Field of the Invention

The present invention relates to scenting mechanisms and more particularly pertains to a new computer game enhancement for affording a scent during the use of a computer or game unit.

2. Description of the Prior Art

The use of scenting mechanisms is known in the prior art. More specifically, scenting mechanisms heretofore devised and utilized are known to consist basically of familiar, expected and obvious structural configurations, notwithstanding the myriad of designs encompassed by the crowded prior art which have been developed for the fulfillment of countless objectives and requirements.

Known prior art scenting mechanisms include U.S. Pat. No. 4,579,261; U.S. Pat. No. 4,407,585; U.S. Pat. No. 5,431,569; U.S. Pat. No. 4,953,763; U.S. Pat. Des. No. 310,480; and U.S. Pat. No. 3,214,062.

In these respects, the computer game enhancement according to the present invention substantially departs from the conventional concepts and designs of the prior art, and in so doing provides an apparatus primarily developed for the purpose of affording a scent during the use of a computer or game unit.

SUMMARY OF THE INVENTION

In view of the foregoing disadvantages inherent in the known types of scenting mechanisms now present in the prior art, the present invention provides a new computer game enhancement construction wherein the same can be utilized for affording a scent during the use of a computer or game unit.

The general purpose of the present invention, which will be described subsequently in greater detail, is to provide a new computer game enhancement apparatus and method which has many of the advantages of the scenting mechanisms mentioned heretofore and many novel features that result in a new computer game enhancement which is not anticipated, rendered obvious, suggested, or even implied by any of the prior art scenting mechanisms, either alone or in any combination thereof.

To attain this, the present invention generally comprises a housing with a rectangular configuration. As shown in the Figures, the housing has a square front face, a square rear face and a side wall integrally coupled therebetween defined by four elongated rectangular faces. As such, an interior space is formed with a constant square cross-section along an entire length thereof. The front and rear faces of the housing each have a circular bore formed in a center thereof. Associated therewith is a cylindrical threaded sleeve mounted to an outer surface of the front or rear face in concentric relationship with the associated bore. Each sleeve extends outwardly from the corresponding face with a plurality of threaded grooves formed on an outer surface thereof. With reference now to FIG. 3, the housing is shown to include a divider with a size and shape similar to that of the front and rear faces. Such divider is integrally coupled within the interior space of the housing at a central extent of the side wall. For reasons that will soon become apparent, the divider has an aperture formed in a central extent thereof. Also included is a pair of conduits each having a cylindrical configuration. As shown in FIG. 3, the conduits include an input conduit with a first end sealingly coupled to an inner surface of the rear face of the housing in axial alignment with the circular bore thereof. A second end of the input conduit is sealingly coupled to a first face of the divider for providing hermetical communication between the aperture of the divider and the bore of the rear face. The conduits further include an output conduit with a first end sealingly coupled to an inner surface of the front face of the housing in axial alignment with the circular bore thereof. Associated therewith is a second end sealingly coupled to a second face of the divider. By this structure, hermetical communication is afforded between the aperture of the divider and the bore of the front face. Next provided is a scented filter assembly including a tubular shell with a pair of open ends Situated within the shell is a scented filter materiel for dispensing a scent upon the flow of air therethrough. It should be noted that the scented filter assembly is removably inserted within the output conduit. FIG. 3 shows a piercing assembly including a rigid cylindrical sleeve mounted on the first face of the divider in concentric relationship with the aperture. An elastomeric bushing is mounted within the sleeve of the piercing assembly with a disk-shaped recess formed in an end thereof. A pin is situated within the bushing in concentric relationship therewith. A first end of such pin remains in communication with the aperture of the divider while a second end extends from the bushing. Removably inserted within the input conduit is a compressed air tank with a cylindrical configuration. During use, the air tank is pierced by the pin of the piercing assembly upon the insertion of the same within the input conduit. As such, compressed air is dispensed through the aperture of the divider for being directed through the scented filter assembly. For governing the flow of air through the scenting filter, a solenoid valve is mounted within the divider of the housing. The solenoid has a transducer with an unbiased orientation covering the aperture for precluding the flow of air to the scented filter assembly. The transducer further has a biased orientation for allowing the flow of air to the scented filter assembly only upon the actuation thereof. The solenoid is connected to a cable which exits the housing at the rear face thereof. Such cable terminates at an adapter for releasably connecting with a control means which is adapted to actuate the solenoid valve during a computer game. Finally, a plurality of caps each has a circular face with a peripheral lip coupled to a periphery of the circular face and extended therefrom. A plurality of threaded grooves are formed in an inner surface of the lip of each cap. The caps includes a first cap with a single enlarged bore formed in the circular face thereof for allowing scented air to be directed directly therethrough upon being secured to the threaded sleeve of the front face of the housing. For allowing scented air to be directed from the housing in a dispersed manner, a second cap is equipped with a matrix of small bores formed in the circular face thereof. Finally, a third cap is provided with a closed circular face for being secured to the threaded sleeve of the rear face of the housing. When the third cap is secured, the piercing of the compressed air tank is effected.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new computer game enhancement apparatus and method which has many of the advantages of the scenting mechanisms mentioned heretofore and many novel features that result in a new computer game enhancement which is not anticipated, rendered obvious, suggested, or even implied by any of the prior art scenting mechanisms, either alone or in any combination thereof.

It is another object of the present invention to provide a new computer game enhancement which may be easily and efficiently manufactured and marketed.

It is a further object of the present invention to provide a new computer game enhancement which is of a durable and reliable construction.

An even further object of the present invention is to provide a new computer game enhancement which is susceptible of a low cost of manufacture with regard to both materials and labor, and which accordingly is then susceptible of low prices of sale to the consuming public, thereby making such computer game enhancement economically available to the buying public.

Still yet another object of the present invention is to provide a new computer game enhancement which provides in the apparatuses and methods of the prior art some of the advantages thereof, while simultaneously overcoming some of the disadvantages normally associated therewith.

Still another object of the present invention is to provide a new computer game enhancement for affording a scent during the use of a computer or game unit.

Even still another object of the present invention is to provide a new computer game enhancement that includes a scenting mechanism for dispensing a scent upon the actuation thereof. Further included is an actuation mechanism connected between the scenting mechanism and either a computer or a game unit for actuating the scenting mechanism during a game.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
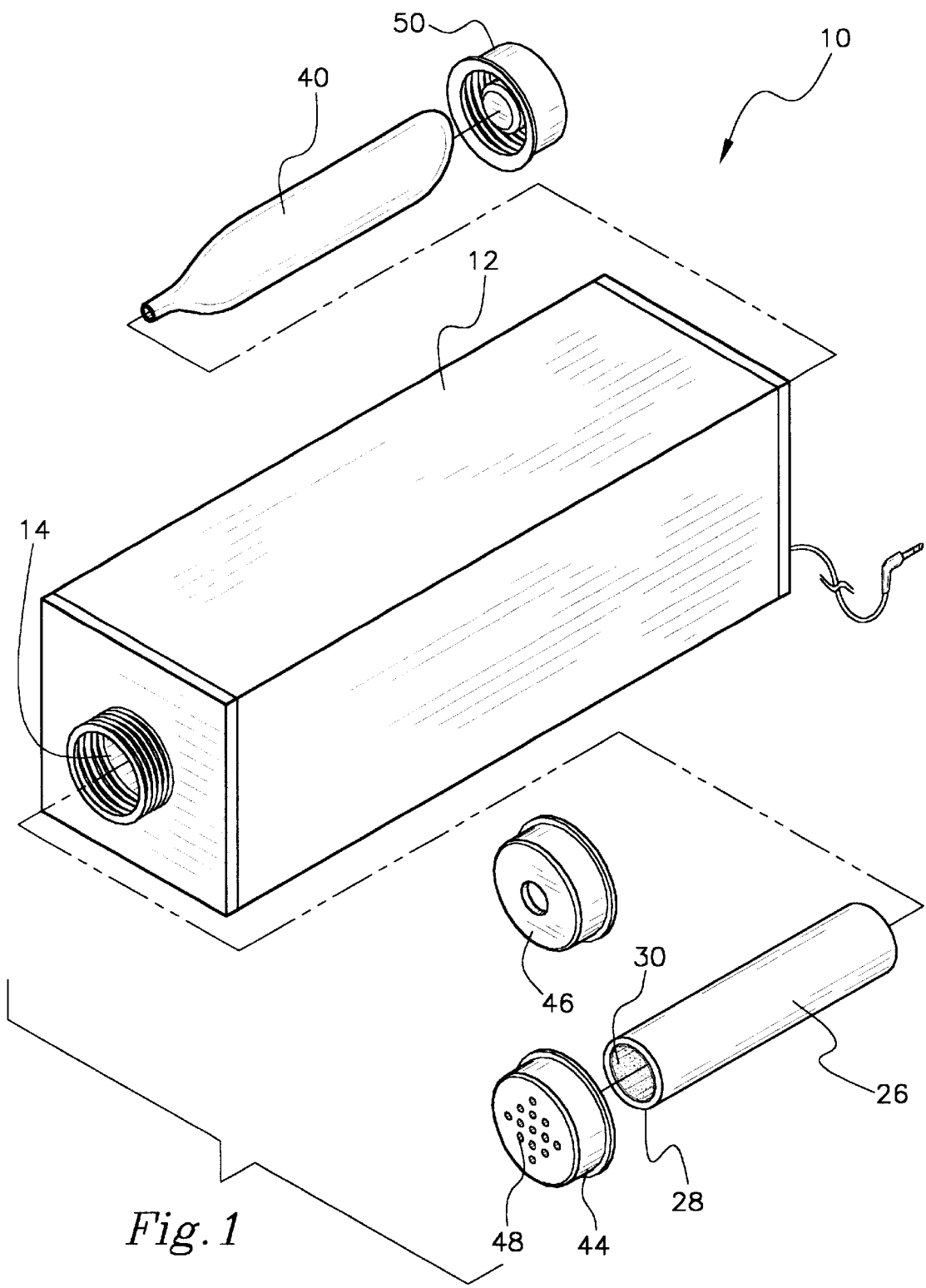
FIG. 1 is an exploded perspective view of a new computer game enhancement according to the present invention.
Figure 2:
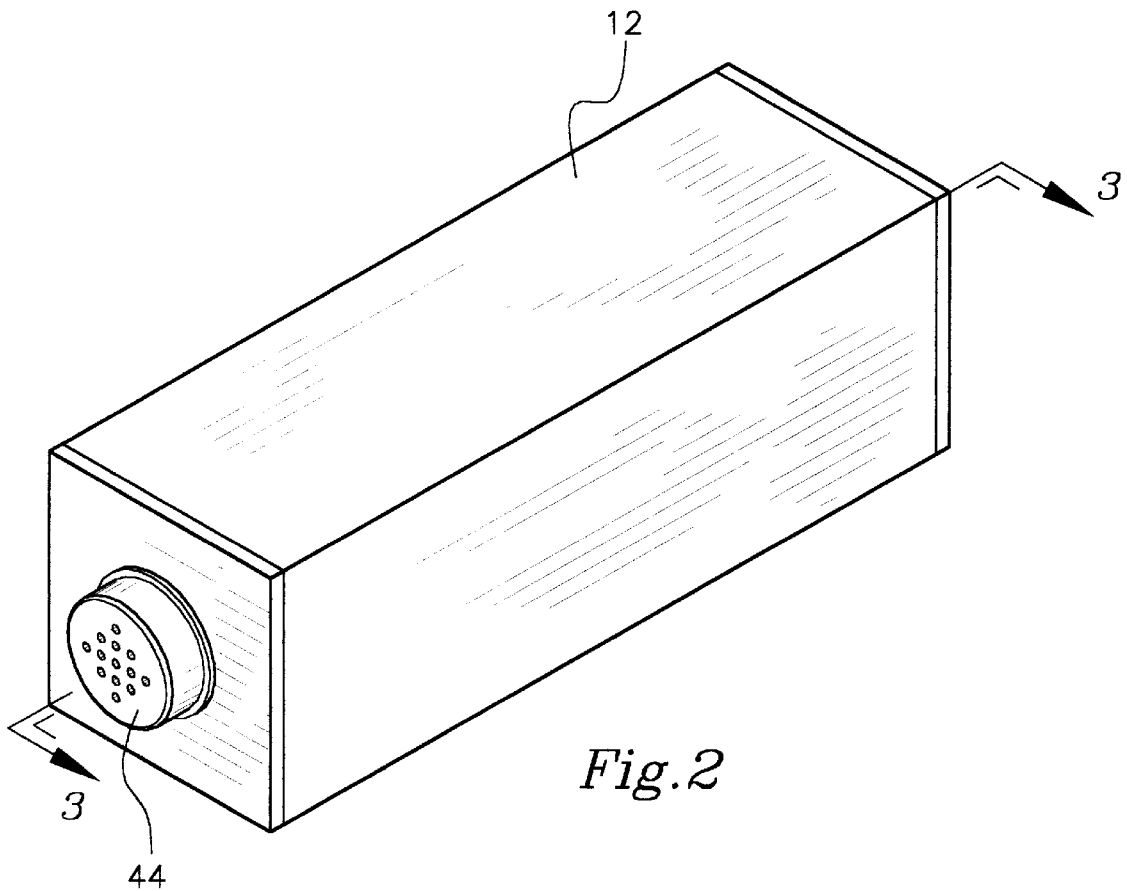
FIG. 2 is a perspective view of the present invention.
Figure 3:
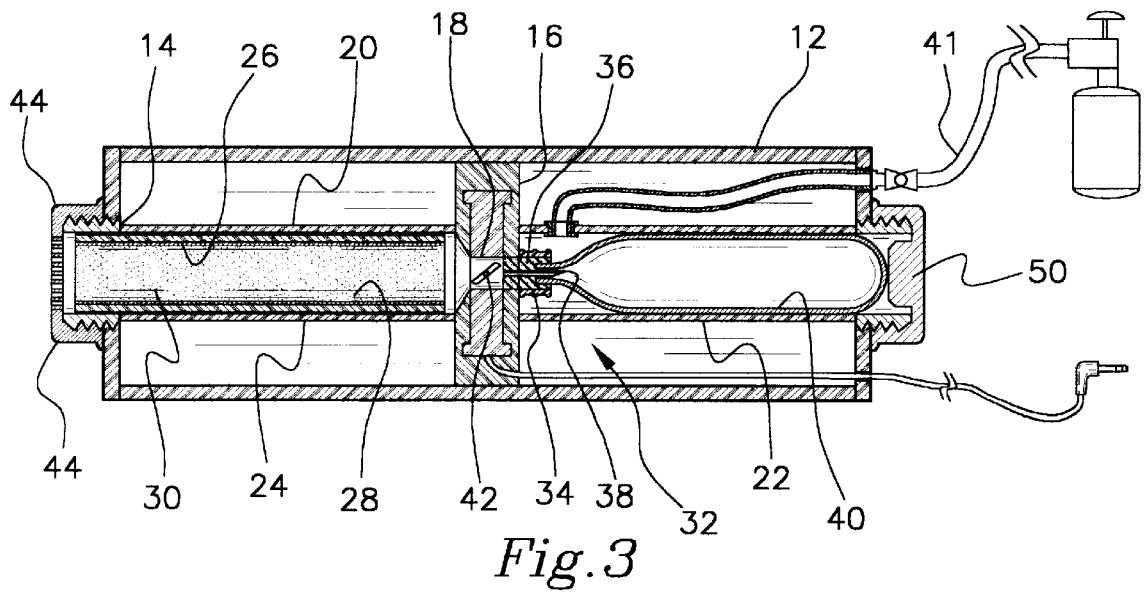
FIG. 3 is a side cross-sectional view of the present invention taken along line 3—3 shown in FIG. 2.

With reference now to the drawings, and in particular to FIGS. 1 through 3 thereof, a new computer game enhancement embodying the principles and concepts of the present invention and generally designated by the reference numeral 10 will be described.

The present invention, designated as numeral 10, includes a housing 12 with a rectangular configuration. As shown in the Figures, the housing has a square front face, a square rear face and a side wall integrally coupled therebetween defined by four elongated rectangular faces. As such, an interior space is formed with a constant square cross-section along an entire length thereof. The front and rear faces of the housing each have a circular bore 14 formed in a center thereof. Associated therewith is a cylindrical threaded sleeve mounted to an outer surface of the front and rear face in concentric relationship with the associated bore. Each sleeve extends outwardly from the corresponding face with a plurality of threaded grooves formed on an outer surface thereof.

With reference now to FIG. 3, the housing is shown to include a divider 16 with a size and shape similar to that of the front and rear faces. Such divider is integrally coupled within the interior space of the housing at a central extent of the side wall. For reasons that will soon become apparent, the divider has an aperture 18 formed in a central extent thereof.

Also included is a pair of conduits 20 each having a cylindrical configuration. As shown in FIG. 3, the conduits include an input conduit 22 with a first end sealingly coupled to an inner surface of the rear face of the housing in axial alignment with the circular bore thereof. A second end of the input conduit is sealingly coupled to a first face of the divider for providing hermetical communication between the aperture of the divider and the bore of the rear face. The conduits further include an output conduit 24 with a first end sealingly coupled to an inner surface of the front face of the housing in axial alignment with the circular bore thereof. Associated therewith is a second end sealingly coupled to a second face of the divider. By this structure, hermetical communication is afforded between the aperture of the divider and the bore of the front face. As shown in FIG. 3, the conduits are preferably situated in coaxial alignment.

Next provided is a scented filter assembly 26 including a tubular shell 28 with a pair of open ends. Situated within the shell is a scented filter materiel 30 for dispensing a scent upon the flow of air therethrough. Such scent may take the form of any sort including bodily smells, burning rubber, burning fuel or the like. It should be noted that the scented filter assembly is removably inserted within the output conduit.

FIG. 3 shows a piercing assembly 32 including a rigid cylindrical sleeve 34 mounted on the first face of the divider in concentric relationship with the aperture. An elastomeric bushing 36 is mounted within the sleeve of the piercing assembly with a disk-shaped recess formed in an end thereof. A pin 38 is situated within the bushing in concentric relationship therewith. A first end of such pin remains in communication with the aperture of the divider whereas a second end extends from the bushing.

Removably inserted within the input conduit is a compressed air tank 40 with a cylindrical configuration. During use, the air tank is pierced by the pin of the piercing assembly upon the insertion of the same within the input conduit. As such, compressed air is dispensed through the aperture of the divider for being directed through the scented filter assembly.

To provide an alternate air supply, a tube 41 is included having a first end mounted on a periphery of the input conduit and a second end extending from the rear face of the housing for connecting with an external air supply. A one-way valve may be mounted on the tube for preventing a backflow of air.

For governing the flow of air through the scenting filter, a solenoid valve 42 is mounted within the divider of the housing. The solenoid has a transducer with an unbiased orientation covering the aperture for precluding the flow of air to the scented filter assembly. The transducer further has a biased orientation for allowing the flow of air to the scented filter assembly only upon the actuation thereof. The solenoid is connected to a cable which exits the housing at the rear face thereof. Such cable terminates at an adapter for releasably connecting with a control means such as a computer or game unit via a sound card. In use, such control means is adapted to actuate the solenoid valve during a computer game so as to simulate a more realistic playing environment. As an option, the solenoid valve may be manually actuated by way of a hot key on an associated keyboard.

Finally, a plurality of caps 44 each has a circular face with a peripheral lip coupled to a periphery of the circular face and extended therefrom. A plurality of threaded grooves are formed in an inner surface of the lip of each cap. The caps includes a first cap 46 with a single enlarged bore formed in the circular face thereof for allowing scented air to be directed directly therethrough upon being secured to the threaded sleeve of the front face of the housing. For allowing scented air to be directed from the housing in a dispersed manner, a second cap 48 is equipped with a matrix of small bores formed in the circular face thereof. Finally, a third cap 50 is provided with a closed circular face for being hermetically secured to the threaded sleeve of the rear face of the housing. When the third cap is secured, the piercing of the compressed air tank is effected.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification ire intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A computer actuated scent apparatus comprising, in combination:

a housing with a rectangular configuration having a square front face, a square rear face and a side wall integrally coupled therebetween defined by four elongated rectangular faces, thereby forming an interior space with a constant square cross-section along an entire length thereof, the front and rear faces each having a circular bore formed in a center thereof and a cylindrical threaded sleeve mounted to an outer surface thereof in concentric relationship with the associated bore and extending outwardly therefrom with a plurality of threaded grooves formed on an outer surface thereof, the housing further including a divider with a size and shape similar to that of the front and rear faces, the divider integrally coupled within the interior space of the housing at a central extent of the side wall, wherein the divider has an aperture formed in a central extent thereof;

a pair of conduits each having a cylindrical configuration, the conduits including an input conduit with a first end sealingly coupled to an inner surface of the rear face of the housing in axial alignment with the circular bore thereof and a second end sealingly coupled to a first face of the divider for providing hermetical communication between the aperture of the divider and the bore of the rear face, the conduits further including an output conduit with a first end sealingly coupled to an inner surface of the front face of the housing in axial alignment with the circular bore thereof and a second end sealingly coupled to a second face of the divider for providing hermetical communication between the aperture of the divider and the bore of the front face;

a scented filter assembly including a tubular shell with a pair of open ends and a scented filter materiel situated within the shell for dispensing a scent upon the flow of air therethrough, wherein the scented filter assembly is removably inserted within the output conduit;

a piercing assembly including a rigid cylindrical sleeve mounted on the first face of the divider in concentric relationship with the aperture, an elastomeric bushing mounted within the sleeve of the piercing assembly with a disk-shaped recess formed in an end thereof, and a pin mounted within the bushing in concentric relationship therewith with a first end in communication with the aperture of the divider and a second end extending from the bushing;

a compressed air tank with a cylindrical configuration removably inserted within the input conduit, whereby the air tank is pierced by the pin of the piercing assembly upon the insertion of the same within the input conduit such that compressed air is dispensed through the aperture of the divider for being directed through the scented filter assembly;

a solenoid valve mounted within the divider of the housing and having a transducer with an unbiased orientation covering the aperture for precluding the flow of air to the scented filter assembly and a biased orientation for allowing the flow of air to the scented filter assembly only upon the actuation thereof, wherein the solenoid is connected to a cable which exits the housing at the rear face thereof and terminates at an adapter for releasably connecting with a control means which is adapted to actuate the solenoid valve during a computer game; and a plurality of caps each having a circular face with a peripheral lip coupled to a periphery of the circular face and extending therefrom with a plurality of threaded grooves formed in an inner surface thereof, the caps including a first cap with a single enlarged bore formed in the circular face thereof for allowing scented air to be directed directly therethrough upon being secured to the threaded sleeve of the front face of the housing, a second cap with a matrix of small bores formed in the circular face thereof for allowing scented air to be directed therethrough in a dispersed manner upon being secured to the threaded sleeve of the front face of the housing and a third cap with a closed circular face for being secured to the threaded sleeve of the rear face of the housing to effect the piercing of the compressed air tank.

2. A scent apparatus comprising:

scenting means for dispensing a scent upon the actuation thereof;

wherein the scenting means includes an air supply means for supplying air, the air supply means including a compressed air tank wherein the air from the air supply means is scented upon the actuation of the scenting means;

a piercing assembly including a rigid cylindrical sleeve with an elastomeric bushing mounted in the sleeve of the piercing assembly, a pin being mounted in the bushing in concentric relationship with the bushing, the pin having a first end and a second end, the second end extending from the bushing such that the air tank is piercable by the pin of the piercing assembly; and actuation means connected between the scenting means and at least one of a computer and a game unit for actuating the scenting means during a game.

3. A scent apparatus as set forth in claim 2 wherein the scenting means includes a scented filter for scenting air which flows therethrough, wherein the air tank is connected to the scented filter.

4. A scent apparatus as set forth in claim 3 wherein the scented filter and the air tank are situated within a common housing.

5. A scent apparatus as set forth in claim 2 wherein the scenting means includes an air flow scenting means for scenting air which flows therethrough, wherein further included is a plurality of caps for selectively governing such flow of air from the air flow scenting means.

6. A scent apparatus as set forth in claim 2 wherein the scenting means includes an air flow scenting means for scenting air which flows therethrough and a supply of air, wherein the actuation means includes a solenoid valve.

* * * * *